US008919202B2

(12) United States Patent
Keely et al.

(10) Patent No.: US 8,919,202 B2
(45) Date of Patent: Dec. 30, 2014

(54) SYSTEM AND METHOD FOR MONITORING HEALTH OF STATOR VANES

(75) Inventors: Bhasker Rao Keely, Bangalore (IN); Aninda Bhattacharya, Bangalore (IN); Ravi Yoganatha Babu, Bangalore (IN); Nilesh Tralshawala, Rexford, NY (US)

(73) Assignee: General Electric Company, Niskayuna, NY (US)

( * ) Notice: Subject to any disclaimer, the term of this patent is extended or adjusted under 35 U.S.C. 154(b) by 355 days.

(21) Appl. No.: 13/460,000

(22) Filed: Apr. 30, 2012

(65) Prior Publication Data

US 2012/0245860 A1 Sep. 27, 2012

Related U.S. Application Data

(63) Continuation-in-part of application No. 12/756,585, filed on Apr. 8, 2010.

(51) Int. Cl.
*G01N 29/14* (2006.01)
*G06F 19/00* (2011.01)
*F01D 17/02* (2006.01)
*F01D 21/00* (2006.01)
*F01D 21/14* (2006.01)
*F04D 27/00* (2006.01)
*F04D 29/54* (2006.01)

(52) U.S. Cl.
CPC .............. *F01D 17/02* (2013.01); *F01D 21/003* (2013.01); *F01D 21/14* (2013.01); *F04D 27/001* (2013.01); *F04D 29/542* (2013.01)
USPC .................... 73/649; 73/587; 73/602; 702/35

(58) Field of Classification Search
USPC .................................... 73/649, 587, 593, 602
See application file for complete search history.

(56) References Cited

U.S. PATENT DOCUMENTS 4,429,578 A * 2/1984 Darrel et al. ..................... 73/659
5,445,027 A * 8/1995 Zorner ............................ 73/593
(Continued)

FOREIGN PATENT DOCUMENTS

EP 2375081 A2 10/2011
JP 0712709 A 1/1995
(Continued)

OTHER PUBLICATIONS

David Mba et al., "Development of Acoustic Emission Technology for Condition Monitoring and Diagnosis of Rotating Machines; Bearings, Pumps, Gearboxes, Engines and Rotating Structures", The Shock and Vibration Digest, vol. 38(1),2006, pp. 3-16.

(Continued)

*Primary Examiner* — J M Saint Surin
(74) *Attorney, Agent, or Firm* — Ann M. Agosti

(57) ABSTRACT

A system including a plurality of sensing devices configured to generate acoustic emission (AE) signals that are representative of acoustic emission waves propagating through a plurality of stator vanes is presented. The system further includes a processing subsystem that is in an operational communication with the plurality of sensing devices, and the processing subsystem is configured to generate a dynamic threshold based upon an initial threshold and the AE signals, determine whether a plurality of signals of interest exist in the AE signals based upon the dynamic threshold, extract the plurality of signals of interest from the AE signals based upon the dynamic threshold, determine one or more features corresponding to the plurality of signals of interest, and analyze the one or more features to monitor and validate the health of the plurality of stator vanes.

20 Claims, 6 Drawing Sheets

(56) References Cited

U.S. PATENT DOCUMENTS

| | | | |
|---|---|---|---|
| 7,987,725 B2 * | 8/2011 | Twerdochlib | 73/661 |
| 8,074,499 B2 * | 12/2011 | Kinzie et al. | 73/112.01 |
| 8,631,704 B2 * | 1/2014 | Guy | 73/577 |
| 2002/0190721 A1 | 12/2002 | Harrold et al. | |
| 2003/0077179 A1 * | 4/2003 | Collins et al. | 417/63 |

FOREIGN PATENT DOCUMENTS

| | | |
|---|---|---|
| JP | 9145340 A | 6/1997 |
| JP | 9195795 A | 7/1997 |
| JP | 9250990 A | 9/1997 |
| JP | 2004077357 A | 3/2004 |

OTHER PUBLICATIONS

Champaigne et al., "Low-power Electronics for Distributed Impact Detection and Piezoelectric Sensor Applications", IEEE Aerospace Conference Proceedings, 2007, pp. 1-8.

EPO Search Report Dated Aug. 29, 2013; GE Reference No. 257803/19418Application No. 13165626.6-1557; 5 Pages.

\* cited by examiner

SYSTEM AND METHOD FOR MONITORING HEALTH OF STATOR VANES

CROSS REFERENCE TO RELATED APPLICATIONS

This application is a continuation-in-part of U.S. patent application Ser. No. 12/756,585, entitled "System And Method For Monitoring a compressor", filed on Apr. 8, 2010, which is herein incorporated by reference.

BACKGROUND

The present disclosure generally relates to systems and methods for monitoring health of stationary blades or stator vanes.

A gas turbine may include an axial compressor at the front, one or more combustors around the middle, and a turbine at the rear. Typically, an axial compressor has a series of stages with each stage comprising a row of rotor blades or airfoils followed by a row of static blades or static airfoils. Accordingly, each stage comprises a pair of rotor blades or airfoils and static airfoils. Typically, the rotor blades or airfoils increase the kinetic energy of a fluid that enters the axial compressor through an inlet. Furthermore, the static blades or static airfoils generally convert the increased kinetic energy of the fluid into static pressure through diffusion. Accordingly, the rotor blades or airfoils and static airfoils play a vital role to increase the pressure of the fluid.

Furthermore, the rotor blades or airfoils and the static airfoils are vital due to wide and varied applications of the axial compressors that include the airfoils. Axial compressors, for example, may be used in a number of devices, such as, land based gas turbines, jet engines, high speed ship engines, small scale power stations, or the like. In addition, the axial compressors may be used in varied applications, such as, large volume air separation plants, blast furnace air, fluid catalytic cracking air, propane dehydrogenation, or the like.

Moisture/humidity, high temperatures etcetera in the environment lead to corrosion of various airfoils and other structures inside the gas turbine. This, in combination with low cycle fatigue and high cycle fatigue during operation of the turbine, lead to stress-corrosion cracking, especially, if extreme stress is experienced due to abnormal resonances or impact of foreign objects. Additionally, the airfoils operate for long hours under extreme and varied operating conditions such as, high speed, pressure and temperature that affect the health of the airfoils. In addition to the extreme and varied conditions, certain other factors lead to fatigue and stress of the airfoils. The factors, for example, may include inertial forces including centrifugal force, pressure, excitation of the resonant frequencies of the airfoils, vibrations in the airfoils, vibratory stresses, temperature stresses, reseating of the airfoils, load of the gas or other fluid, or the like. A prolonged increase in stress and fatigue over a period of time leads to defects and cracks in the airfoils. One or more of the cracks may widen with time to result in liberation of an airfoil or a portion of the airfoil. The liberation of airfoil may be hazardous for the device that includes the airfoils, and thus may lead to enormous monetary losses. In addition, it may create an unsafe environment for people near the device and result in serious injuries.

Conventional systems and methods exist to monitor the performance and operation of compressors and the airfoils. For example, vibration sensors may be used to monitor vibrations from the compressors and the airfoils during operations. A change in the frequency or magnitude of existing vibrations may indicate excessive wear and/or crack formation. However, vibration sensors may only detect cracks and other anomalies that are large enough to cause an imbalance and vibration in the compressor. As a result, vibration sensors may not detect small cracks that do not result in a detectable vibration in the stator vanes. Accordingly, it is highly desirable to develop the present systems and methods that monitor the health of the airfoils.

BRIEF DESCRIPTION

A system including a plurality of sensing devices configured to generate acoustic emission (AE) signals that are representative of acoustic emission waves propagating through a plurality of stator vanes is presented. The system further includes a processing subsystem that is in an operational communication with the plurality of sensing devices, and the processing subsystem is configured to generate a dynamic threshold based upon an initial threshold and the AE signals, determine whether a plurality of signals of interest exist in the AE signals based upon the dynamic threshold, extract the plurality of signals of interest from the AE signals based upon the dynamic threshold, determine one or more features corresponding to the plurality of signals of interest, and analyze the one or more features to monitor and validate the health of the plurality of stator vanes.

A method of monitoring the health of a plurality of stator vanes is presented. The method includes the steps of generating acoustic emission (AE) signals that are representative of acoustic emission waves propogating through one or more of the plurality of stator vanes, generating a dynamic threshold based upon an initial threshold and the AE signals, determining whether a plurality of signals of interest exist in the AE signals based upon the dynamic threshold, extracting the plurality of signals of interest from the AE signals based upon the dynamic threshold, determining one or more features corresponding to the plurality of signals of interest, and analyzing the one or more features to monitor the health of the plurality of stator vanes.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
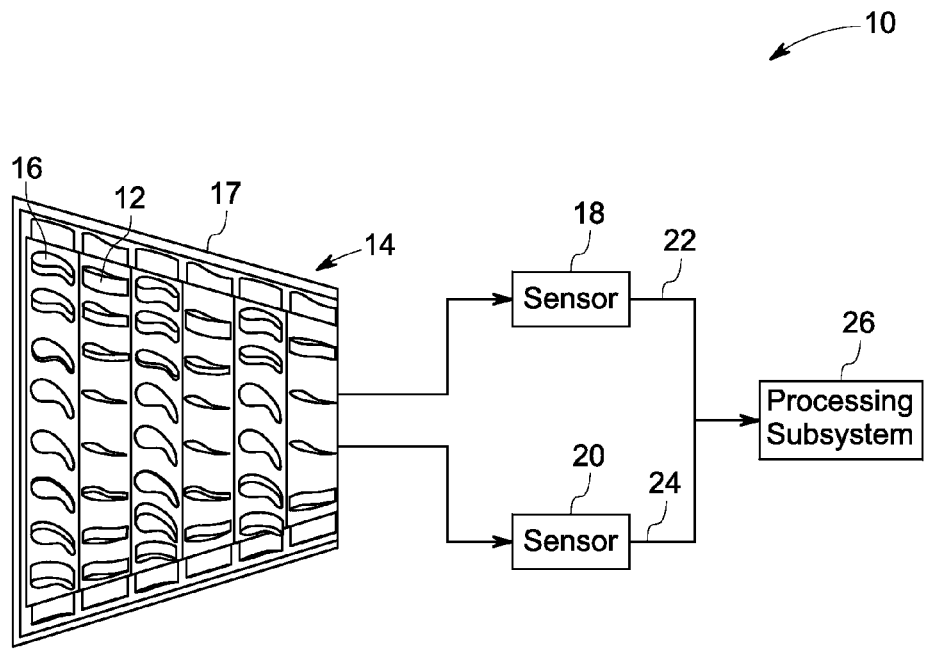
FIG. 1 is a diagrammatic illustration of an exemplary system for monitoring the health of stator vanes, in accordance with certain aspects of the present systems.

FIG. 1 is a diagrammatic illustration of an exemplary system 10 for monitoring the health of stator vanes 12, in accordance with certain aspects of the present systems. Monitoring the health of the stator vanes 12, for example, includes predicting occurrence of cracks and determining cracks in one or more of the stator vanes 12. In one embodiment, monitoring the health of the stator vanes 12 includes determining the length of a crack in one or more of the stator vanes 12. In another embodiment, monitoring the health of the stator vanes 12 includes determining the remaining useful life of the stator vanes 12. It is noted that while the present methods and systems demonstrate monitoring the health of stator vanes, the present methods and systems may be used for monitoring health of stationary blades.

As shown in the presently contemplated configuration, the system 10 includes an axial compressor 14. The axial compressor 14 includes a plurality of rows of rotating blades 16 and the plurality of rows of the stator vanes 12. Each of the plurality of rows of rotating blades 16 is located alternately with respect to each of the rows of stator vanes 12, and vice versa. The system 10 further includes a plurality of sensing devices 18, 20 that are dispersed on the outer surface of a casing 17 that covers the plurality of rows of rotating blades 16 and the plurality of rows of stator vanes 12. The sensing devices 18, 20 may include a magnetostrictive material sensing device, a piezoelectric sensing device, a capacitive sensing device that converts stress waves to electrical signals 22, 24, respectively. The sensing devices 18, 20, for example, may be an optical sensing device, an acoustic emission sensing device, a radio frequency wireless sensing device, or the like.

It is noted that though the present system 10 shows two sensing devices 18, 20, the system 10 may include an optimal number of sensing devices based upon the size of the axial compressor 14 and precision expected in monitoring the stator vanes 12. The location of the plurality sensing devices 18, 20 on the outer surface of the casing 17 is determined using triangulation techniques. The triangulation techniques assist in identifying optimal locations for the sensing devices 18, 20. As used herein, the term "optimal locations for the sensing devices" is herein to refer to locations for distribution of a plurality of sensing devices on the outer surface of a casing of an axial compressor such that AE waves generated by each of the stator vanes 12 is captured by the plurality of sensing devices 18, 20.

When one or more of the stator vanes 12 are operating under stress or under uncharacteristic operating conditions, the one or more of the stator vanes 12 generate acoustic emission (AE) waves. The AE waves travel through different interfaces between the stator vanes 12 and the casing to reach the outer surface of the casing. When these AE waves reach the outer surface of the casing, the sensing devices 18, 20 measure the AE waves to generate the AE signals 22, 24. Each of the AE signals 22, 24 is a time-series signal in voltage. As shown by FIG. 1, the sensing device 18 generates the AE signals 22 and the sensing device 20 generates the AE signals 24. The frequency range of the AE signals 22, 24 vary from about 100 kHz to about 450 kHz.

Furthermore, the system 10 includes a processing subsystem 26 that receives the AE signals 22, 24 from the sensing devices 18, 20. The processing subsystem 26 may include various components, such as, microprocessors, coprocessors, and/or memory/media elements that store data, store software instructions, and/or execute software instructions. The various memory/media elements may be one or more varieties of computer readable media, such as, but not limited to, any combination of volatile memory (e.g., RAM, DRAM, SRAM, etc.), non-volatile memory (e.g., flash drives, hard drives, magnetic tapes, CD-ROM, DVD-ROM, etc.), and/or other memory devices (e.g., diskettes, magnetic based storage media, optical storage media, etc.). Any possible variations of data storage and processor configurations will be appreciated by one of ordinary skill in the art.

In the presently contemplated configuration, the processing subsystem 26 receives the AE signals 22, 24. In certain embodiments, the AE signals 22, 24 may be preprocessed by intermediate devices before reaching the processing subsystem 26. The intermediate devices, for example, may include an amplifier, an interface unit, a data acquisition system, and the like. The initial processing increases the strength and quality of the AE signals 22, 24 before the AE signals 22, 24 are received by the processing subsystem 26. An embodiment of the present systems and techniques where the AE signals 22, 24 are preprocessed before reaching the processing subsystem 26 is explained with reference to FIG. 2.

The processing subsystem 26 receives the AE signals 22, 24 from the sensing devices 18, 20 in real-time. The processing subsystem 26 processes the AE signals 22, 24 to monitor the health of the stator vanes 12. In one embodiment, the processing subsystem 26, is remotely located with respect to the location of the axial compressor 14. In the embodiment, when the processing subsystem 26 is remotely located with respect to the location of the axial compressor 14, the processing subsystem 26 may remotely monitor the health of the stator vanes 12 in real-time without human interference. Therefore, the processing subsystem 26 automatically monitors the health of the stator vanes 12 in real-time. In another embodiment, the processing subsystem 26 may be located in the vicinity of the compressor 14.

The processing of the AE signals 22, 24, for example, includes the step of determining features corresponding to the AE signals 22, 24 followed by analysis of the features. In one embodiment, the features, for example, include time-domain features and frequency-domain features. The time-domain features, for example, include ring down count (RDC), amplitude, event duration (ED), peak amplitude (PA), rise time (RT), energy, or the like. As used herein, the term "ring down count" is used to refer to a number of times an acoustic emission signal crosses a dynamic threshold. As used herein, the term "event duration" is used to refer to a duration between a first time instance when an acoustic emission signal crosses a dynamic threshold and a last time instance when the acoustic emission signal crosses the dynamic threshold. As used herein, the term "rise time" is used to refer to time taken by an acoustic emission wave to travel from its first threshold crossing till peak amplitude in a given waveform. The frequency domain features, for example may include frequency distribution of the power spectral density of AE signals 22, 24, the variations in these distributions, wavelets, and the like. As previously noted, the determination of the features is followed by analysis of the features. The analysis of the features, for example, may be performed using cumulative data analysis techniques. The processing of the AE signals 22, 24, and analysis of the features shall be explained in detail with reference to FIG. 3.

Figure 2:
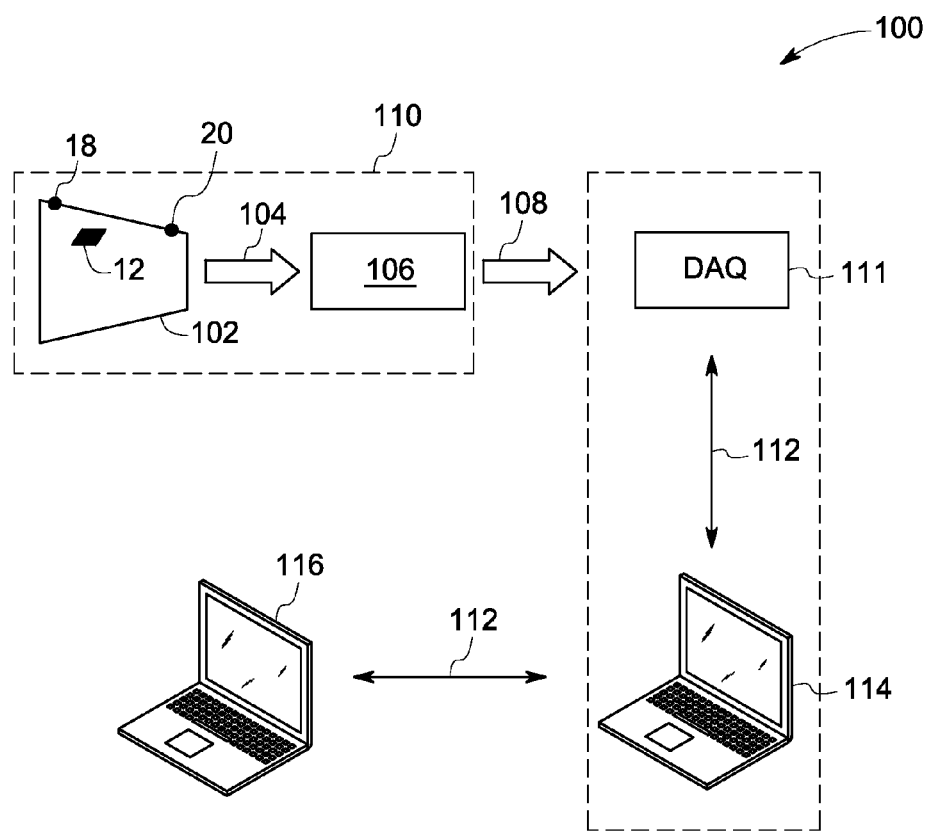
FIG. 2 is a diagrammatic illustration of a system for monitoring the health of stator vanes, in accordance with another embodiment of the present systems.

FIG. 2 is a diagrammatic illustration of a system 100 for monitoring the health of the stator vanes 12, in accordance with another embodiment of the present systems. Particularly, FIG. 2 illustrates preprocessing of AE signals by intermediate devices before the AE signals reach a processing subsystem. The system 100 includes the plurality of sensing devices 18, 20 that are mounted on the outer surface of a casing of a compressor 102. The sensing devices 18, 20 generate AE signals 104 that are representative of stress waves in at least one of the stator vanes 12 in the compressor 102. In the presently contemplated configuration, the sensing devices 18, 20 are physically coupled with an amplification device 106. In the presently contemplated configuration, the amplification device 106 is located in a turbine compartment 110 of the compressor 102. In alternative embodiments, the amplification device 106 may be located outside the turbine compartment 110. The amplification device 106 may be physically coupled with the sensing devices 18, 20 via high temperature cables. The amplification device 106 amplifies the AE signals 104 to improve the strength of the AE signals 104. Consequent to the amplification of the AE signals 104 amplified AE signals 108 are generated.

As shown in FIG. 2, the system 100 further includes a data acquisition system (DAQ) 111. As shown in FIG. 1, the DAQ 111 is operationally coupled with the amplification device 106. The DAQ 111 receives the amplified AE signals 108 and converts the amplified AE signals 108 into AE data 112. In one embodiment, the DAQ 111 may remove noise from the amplified AE signals 108 before converting the amplified AE signals 108 into the AE data 112. The system 100 further includes a first processing subsystem 114. The first processing subsystem 114 may be operationally associated with the DAQ 111. In certain embodiments, the first processing subsystem 114 may be physically connected with the DAQ 111 via low temperature wires. In one embodiment, the first processing subsystem 114 is located in the vicinity of the DAQ 111. In another embodiment, the DAQ 111 may be a part of the first processing subsystem 114. In alternative embodiments, the first processing subsystem 114 may perform the functions of the DAQ 111, and therefore, the DAQ 111 may not exist in the system 100.

The first processing subsystem 114 receives the AE data 112 from the DAQ 111, and monitors the health of the stator vanes 12 in real time by processing the AE data 112. The first processing subsystem 114 processes the AE data 112 to determine features corresponding to the AE data 112. The features, for example, may include ring down count (RDC), amplitude, event duration (ED), peak amplitude (PA), rise time (RT), energy, frequency distribution of the power spectral density, frequency, and the like. Subsequently, the first processing subsystem 114 analyzes the features to monitor the health of the stator vanes 12. The system 100 further includes a second processing subsystem 116 that is located at a remote location with respect to the locations of the compressor 102 and the first processing subsystem 114. The second processing subsystem 116 is operationally associated with the first processing subsystem. In one embodiment, the second processing subsystem 116 may be connected via. a wireless medium or a wired medium with the first processing subsystem 114.

The second processing subsystem 116 is configured to enable a user to access the first processing subsystem 114. Therefore, the second processing subsystem 114 may be used by a user to monitor the health of the stator vanes 12 from a remote location. Particularly, the second processing subsystem 116 enables a user to review monitoring results and intermediate processing results, and results related to analysis of features generated by the first processing subsystem 114.

Figure 3:
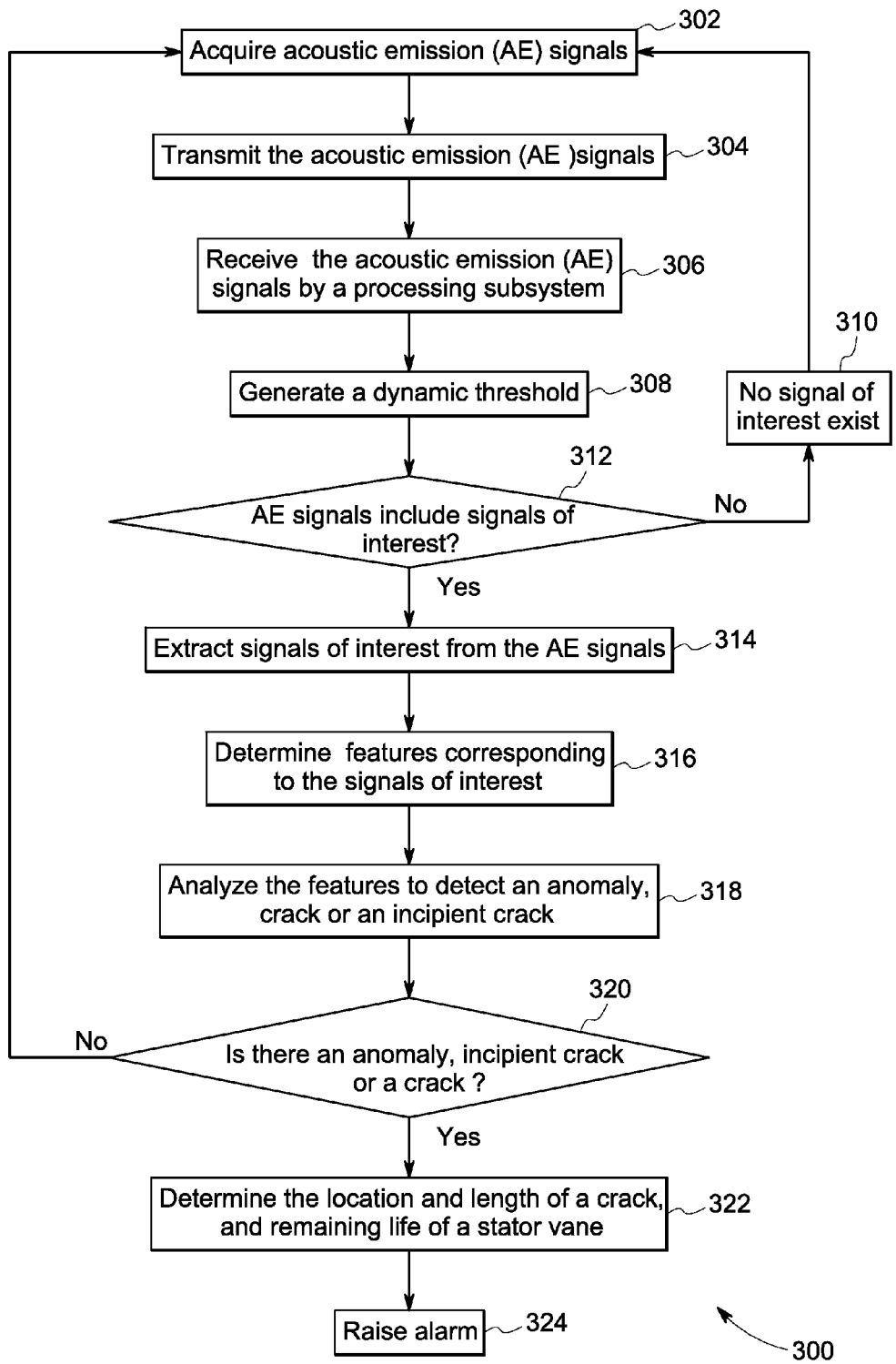
FIG. 3 is an exemplary flow diagram for monitoring the health of a stator vane, in accordance with an embodiment of the present techniques.

FIG. 3 is an exemplary flow diagram 300 for monitoring the health of a stator vane, in accordance with an embodiment of the present techniques. As shown in FIG. 3, the method starts at step 302 where AE signals are acquired. The AE signals may be the acoustic emission (AE) signals 22, 24, 104 as referred to in FIG. 1 and FIG. 2. The AE signals, for example, may be acquired by the plurality of sensing devices 18, 20 as referred in FIG. 1 and FIG. 2. The frequency range of the AE signals vary from about 100 kHz to about 450 kHz. Furthermore, at step 304 the AE signals may be transmitted to a processing subsystem, such as the processing subsystem 26, the first processing subsystem 114, or the second processing subsystem 116.

At step 306, the AE signals are received by the processing subsystem. It is noted that in certain embodiments, between the steps 304 and 306 the AE signals may be preprocessed by intermediate devices, such as, an amplification device, a data acquisition device, or the like. The preprocessing increases the strength and quality of the AE signals. Subsequently, at step 308, dynamic threshold corresponding to the AE signals may be determined utilizing the AE signals and an initial threshold. As used herein, the term "dynamic threshold" refers to a threshold that is determined in real-time to identify acoustic emission events. The acoustic emission events, for example, may include a crack, an anomaly, an incipient crack, or the like. The dynamic threshold, for example, may be determined by the processing subsystem 26, the first processing subsystem 114, or the second processing subsystem 116. In certain embodiments, the dynamic threshold may be determined by the DAQ 111. The determination of the dynamic threshold utilizing AE signals and an initial threshold is explained in detail with reference to FIG. 4.

Subsequent to the determination of the dynamic threshold, at step 312 a check is carried out to verify whether the AE signals include one or more signals of interest. Particularly, the check is carried out by verifying whether one or more portions of the AE signals exceed the dynamic threshold. The check is carried out by comparing the AE signals with the dynamic threshold. At step 312, when it is verified that one or more portions of the AE signals exceeds the dynamic threshold, the control is transferred to step 314. At step 314, at least one signal of interest is extracted from of the AE signals. In one embodiment, a signal of interest is extracted by clipping a portion of an AE signal starting at the first instance the AE signal exceeds the dynamic threshold till a predetermined time period. As used herein, the term "signal of interest" refers to a portion of an AE signal that is extracted based upon a dynamic threshold. The extraction of the signal of interest based upon the dynamic threshold helps in distinguishing AE signals that are generated due to crack propagation/initiation or anomaly from AE signals that are generated due to operational noise generated during compressor or turbine operation. Extraction of a signal of interest from an AE signal in accordance with one embodiment is explained in greater detail in FIG. 5A and FIG. 5B.

Figure 5A:
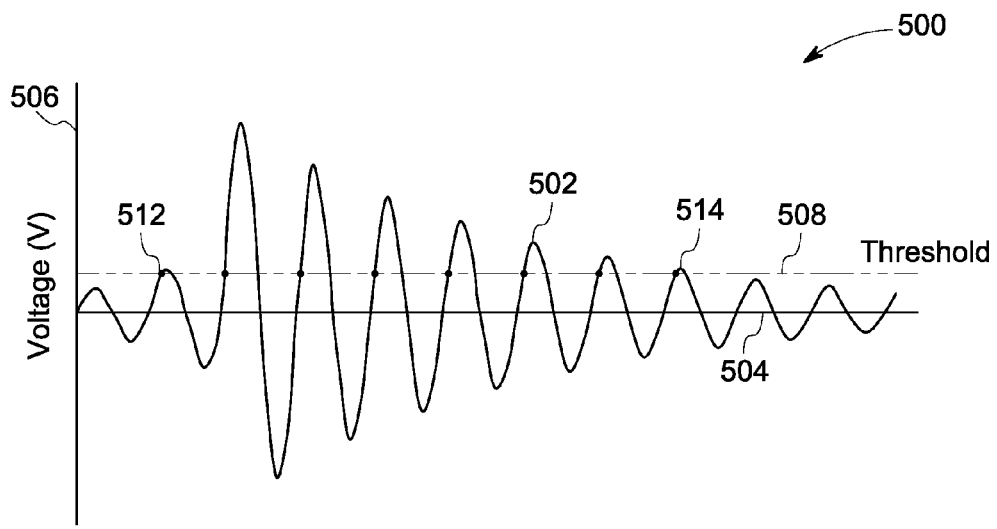
FIG. 5A and FIG. 5B show extraction of a signal of interest from an exemplary profile of an AE signal in accordance with one embodiment.
Figure 5B:
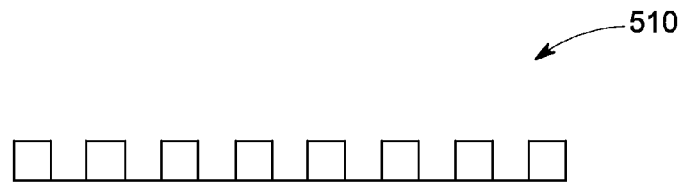

Turning now to FIG. 5A and FIG. 5B, these figures show extraction of a signal of interest from an exemplary profile 500 of an AE signal 502 in accordance with one embodiment. Particularly, FIG. 5A and FIG. 5B explain the step 314 in FIG. 3 in greater detail. X-axis 504 is representative of time, and Y-axis 506 is representative of voltage. Reference numeral 508 is representative of a dynamic threshold that is used to extract a signal of interest 510. As shown in the presently contemplated configuration, the AE signal 502 exceeds the dynamic threshold 508 at a first instance at a location 512. Furthermore, the AE signal 502 exceeds the dynamic threshold till the location 514. Accordingly, a portion of the AE signal 502 that does not exceed the dynamic threshold 508 starting from the location 512 till the location 514 is extracted. The extraction of the portion of the AE signal 502 results in the signal of interest 510.

With returning reference to FIG. 3, at step 314, signals of interest are extracted from the AE signals. Subsequent to the extraction of the signals of interest, at step 316 one or more features corresponding to each of the signals of interest is determined. The features, for example may include ring down count (RDC), amplitude, event duration (ED), peak amplitude (PA), rise time (RT), energy, frequency distribution of the power spectral density, frequency, and the like. Furthermore, at step 318 the one or more features are analyzed to monitor the health of the stator vane. For example, the one or more features are analyzed to determine an anomaly, a crack or an incipient crack in the stator vane. The features, for example, are analyzed by using cumulative analysis techniques. An exemplary cumulative analysis of amplitude is shown in FIG. 6.

Figure 6:
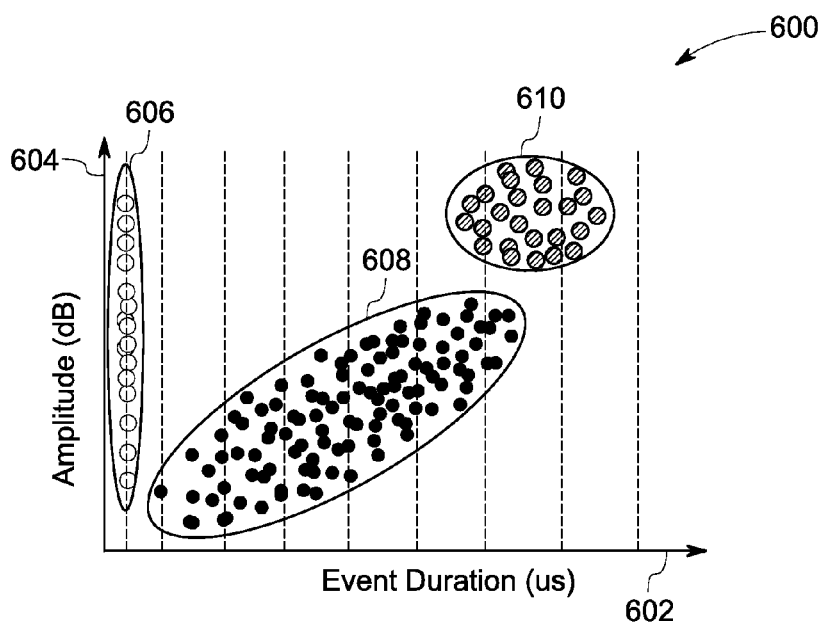
FIG. 6 is a graphical representation of exemplary values of a feature and duration to describe cumulative analysis of features, in accordance with one embodiment of the present techniques.

Turning now to FIG. 6, a graphical representation 600 of exemplary values of a feature plotted with respect to event duration is shown to describe cumulative analysis of features, in accordance with one embodiment of the present techniques. It is noted that the graphical representation 600 does not include experimental values, and shows exemplary values. In the presently contemplated example, amplitude values are used to show an exemplary cumulative analysis of features. In the presently contemplated configuration, X-axis 602 is representative of event duration in milliseconds and Y-axis 604 is representative of amplitude. For exemplary purposes, the values of amplitude have been shown as clustered into three clusters 606, 608, 610. The amplitude values, for example, may be clustered into the three clusters 606, 608, 610 using pattern recognition algorithms, such as, a k-nearest neighbor algorithm. The three clusters 606, 608, 610 show three different scenarios in which amplitude values may get clustered. For example, the cluster 606 shows high amplitude for short event duration. Such cluster 606 that shows high amplitude for short event duration may be characterized to represent noise in AE signals. The cluster 608 shows medium amplitude for larger event duration. Such cluster 608 may be characterized to represent rubbing. Additionally, the cluster 610 shows medium amplitude and even larger event duration, and therefore may be characterized as an anomaly in a stator vane. Such cluster 610 may be characterized to represent a crack in a stator vane. Accordingly, in accordance with one embodiment of the present techniques, when amplitude values corresponding to AE signals result in formation of a cluster that has medium amplitude and large event duration, it may be deduced that one or more stator vanes have a crack.

Turning back to FIG. 3, in certain embodiments, at step 318 the features may be analyzed by comparing one or more of the features against a determined corresponding threshold. For example, the feature amplitude may be compared against an amplitude threshold to determine an anomaly in the stator vane. As used herein, the term "amplitude threshold" refers to a benchmark value of amplitude that may be used to determine an anomaly, an incipient crack or a crack in a stator vane. For, example, when the value of amplitude exceeds the value of a determined amplitude threshold, it may be indicative of a crack in the stator vanes. The analysis of the features in accordance with one embodiment is explained in detail with reference to FIG. 7.

Subsequently at step 320, a check may be carried out to determine whether there is an anomaly, an incipient crack or a crack in the stator vane. The check, for example, may be carried out based upon the analysis of the features. At step 320 when it is verified that an anomaly, incipient crack or crack is present in the stator vane, the control is transferred to step 322. In certain embodiments, at step 322, the location and the length of the crack may be determined. In certain embodiments, at 322, remaining life of a stator vane may be determined. The remaining life of the stator vane, for example, may be determined by identifying when a determined length of crack will reach its maximum crack length in predefined operating conditions. As used herein, the term "maximum crack length" may be used to refer to a critical crack length beyond which an increase in the crack length will lead to liberation of the stator vane. The determination of the length of a crack will be explained in detail with reference to FIG. 8. The determination of the location of a crack is explained in detail with reference to FIG. 9.

Furthermore, at step 324, an alarm may be raised. The alarms may include various categories of alarms based on severity of the anomaly or the length of a crack. For example, in one embodiment, when the analysis of the features shows a large crack in a stator vane, then the alarm may be Red. However, in another embodiment, the analysis of the features shows an anomaly but not a crack, then the alarm may be a yellow alarm. In certain embodiments, when the analysis of the features does not show an anomaly, an incipient crack or a crack, then the alarm may be a green alarm. However, in one embodiment, when the analysis of the features does not show an anomaly, an incipient crack or a crack, then the control may be transferred to step 302. With returning reference to step 312, when it is determined that a signal of interest does not exist, then the control is transferred to step 310. At step 310, it may be declared that a signal of interest does not exist.

Figure 4:
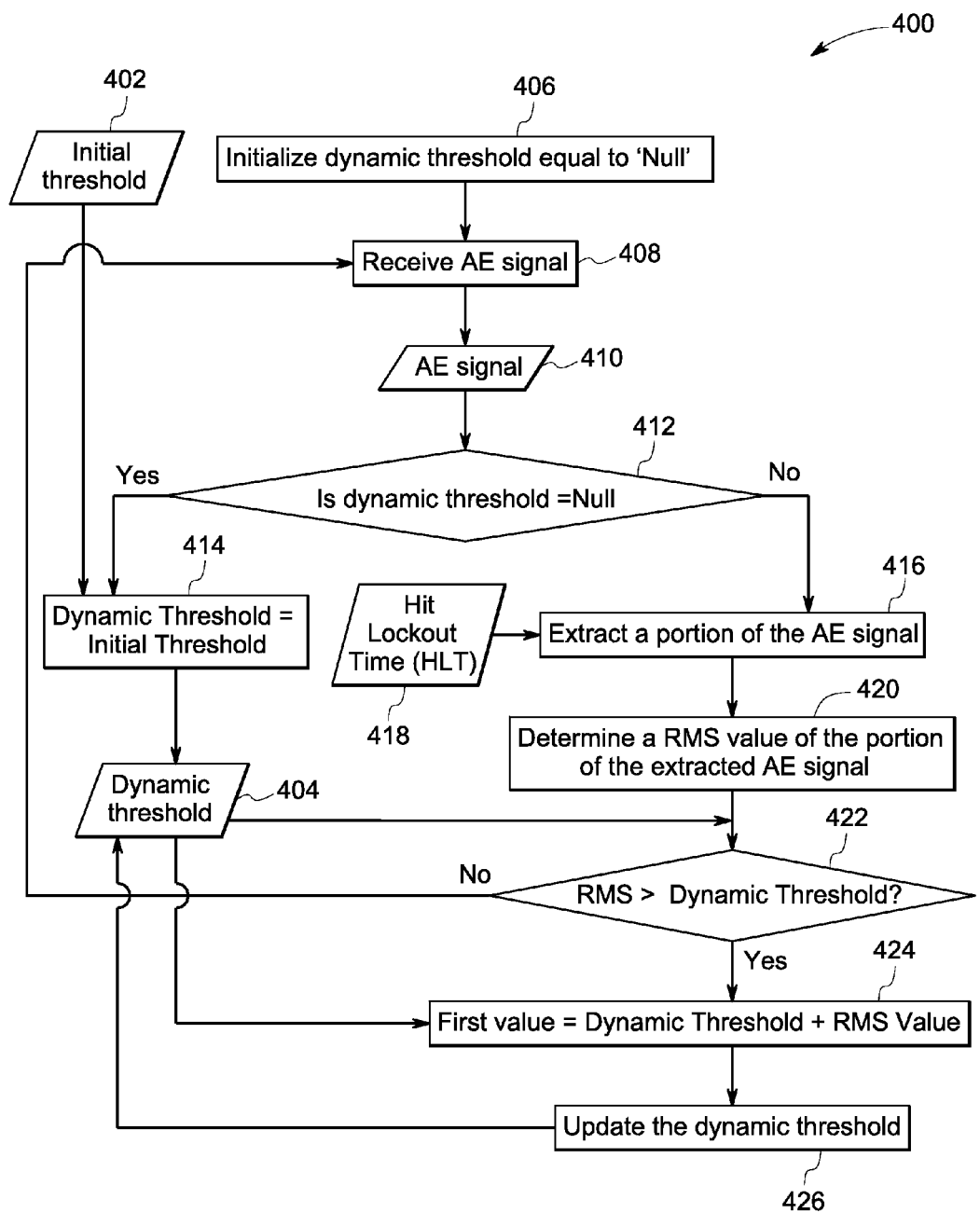
FIG. 4 is an exemplary flow diagram for determining dynamic threshold, in accordance with an embodiment of the present techniques.

FIG. 4 is an exemplary flow diagram 400 for determining dynamic threshold, in accordance with an embodiment of the present techniques. In one embodiment, FIG. 4 explains step 308 in FIG. 3 in greater detail. As shown in FIG. 4, reference numeral 402 is representative of an initial threshold and reference numeral 404 is representative of a dynamic threshold. The initial threshold 402 is preset by a user based upon historical experience, specific model of the compressor and turbine, preamplifier configurations, operating conditions and noise in a turbine including stator vanes to be monitored, and the like. At step 406, the dynamic threshold is initialized to 'Null'. Subsequently at step 408, an AE signal 410 may be received. The AE signal 410, for example, is similar to the AE signals 22, 24, 104 referred to in FIG. 1 and FIG. 2. In one embodiment, the AE signals 410 may be one of the AE signals that are generated at step 302 in FIG. 3.

At step 412, a check is carried out to determine whether the dynamic threshold is equal to Null. The check determines whether the method 400 explained in FIG. 4 is executed for the first time or was previously executed. In other words, when the dynamic threshold is equal to Null, it may be deduced that the method 400 is executed for the first time. At step 412 when it is verified that the dynamic threshold is equal to Null, the control is transferred to step 414. At step 414, the value of the initial threshold 402 is assigned to the dynamic threshold 404. However, at step 412, when it is determined that the dynamic threshold 404 is not equal to Null, the control is transferred to step 416. At step 416, a portion of the AE signals 410 is extracted. The portion of the AE signals 410 is extracted based upon a hit lockout time (HLT) 418. Particularly, the portion of the AE signals 410 is extracted till the HLT 418 ends. As used herein, the term "hit lockout time" is used to refer to a duration predetermined by a user till when an AE signal is extracted. For example, if the HLT 418 is one millisecond, then a portion of the AE signal 410 is extracted starting from the beginning of the AE signal 406 till 1 millisecond.

At step 420, a root mean square value (RMS) of the extracted AE signal may be determined. Furthermore, at step 422, a check is carried out to determine whether the RMS value of the extracted AE signal is greater than the dynamic threshold 404. The RMS value of the extracted AE signal may be greater than the dynamic threshold when the amount of noise in the extracted AE signals has varied with respect to the noise in previously extracted AE signals. At step 422, when it is determined that the RMS value of the extracted AE signal is greater than the dynamic threshold, the control is transferred to step 424. At step 424, the RMS value of the extracted AE signal is added to the dynamic threshold 404 to generate a first value. Subsequent to the generation of the first value, at step 426, the dynamic threshold 404 is equated to the first value. In other words, the dynamic threshold 404 is updated to have a value equivalent to the first value.

Figure 7:
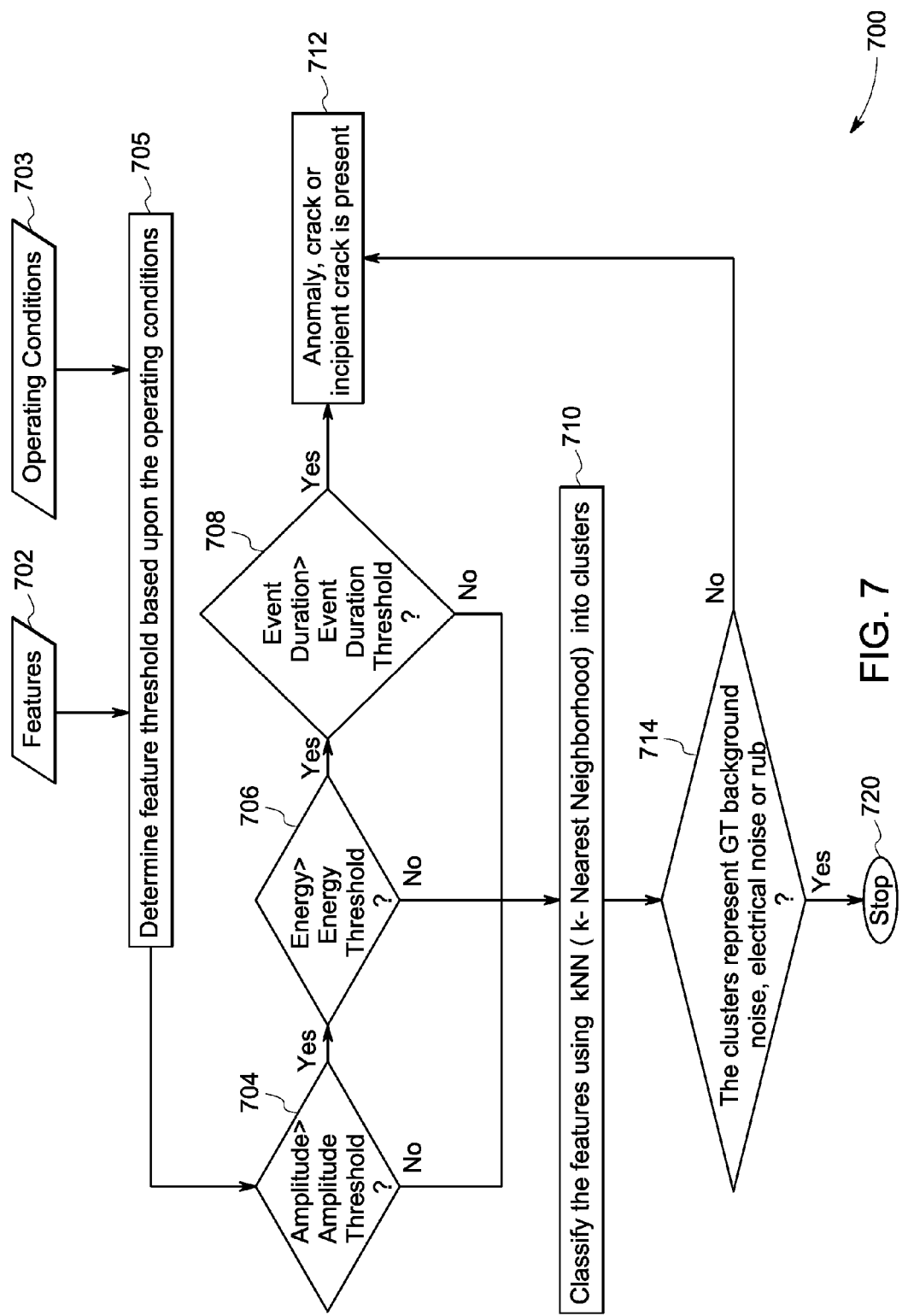
FIG. 7 is an exemplary flow diagram that shows analysis of features, in accordance with an embodiment of the present techniques.

FIG. 7 is an exemplary flow diagram 700 that shows analysis of features 702, in accordance with an embodiment of the present techniques. Reference numeral 702 is representative of features corresponding to signals of interest that are extracted from AE signals. As previously noted with reference to FIG. 1 and FIG. 3, the features 702, for example, may include ring down count (RDC), amplitude, event duration (ED), peak amplitude (PA), rise time (RT), energy, frequency distribution of the power spectral density, frequency, and the like. In the presently contemplated configuration, the features 702 including amplitude, energy and event duration are analyzed. Also, reference numeral 703 is representative of operating conditions of a compressor or turbine. The operating conditions, for example, may include inlet guide vane (IGV) angle, a load variation, reseating of a blade, asynchronous vibration, synchronous vibration, variation of speed, temperature, speed, or the like. At step 705, feature thresholds may be determined based upon the operating conditions 703. As used herein, the term "feature threshold" refers to a benchmark value of feature that may be used to determine an anomaly, an incipient crack or a crack in a stator vane. In FIG. 7, feature thresholds including amplitude threshold, energy threshold and event duration threshold are used to analyze features including amplitude, energy and event duration, respectively. It is noted that though the presently contemplated configuration shows analysis of the features amplitude, energy and event duration, other features may be analyzed using the method 700.

As shown in FIG. 7, at step 704, a check is carried out to determine whether the value of amplitude is greater than the value of the amplitude threshold. As used herein, the term "amplitude threshold" refers to a benchmark value of amplitude that may be used to determine an anomaly, an incipient crack or a crack in a stator vane. It is noted that when the value of amplitude is greater than the amplitude threshold, it may be indicative of an anomaly, an incipient crack or a crack in a stator vane. At step 704, when it is verified that the value of amplitude is greater than the amplitude threshold, the control may be transferred to step 706. However, at step 704, when it is verified that the amplitude is not greater than the amplitude threshold, then the control is transferred to step 710.

At step 706, a check is carried out to verify whether the energy is greater than the energy threshold. As used herein, the term "energy threshold" refers to a benchmark value of energy that may be used to determine an anomaly, an incipient crack or a crack in a stator vane. At step 706, when it is verified that the energy is greater than the energy threshold, then the control is transferred to step 708. It is noted that when the value of amplitude is greater than the energy threshold, it may be indicative of an anomaly, an incipient crack or a crack in a stator vane. However, at step 706, when it is verified that the value of energy is not greater than the energy threshold, then the control is transferred to step 710.

At step 708, a check is carried out to verify whether event duration is greater than the event duration threshold. As used herein the term "event duration" refers to duration between a first time instance when an acoustic emission signal crosses a dynamic threshold and a last time instance when the acoustic emission signal crosses the dynamic threshold. Furthermore, as used herein the term "event duration threshold" is used herein to refer to a benchmark value of event duration that may be used to determine an anomaly, an incipient crack or a crack in a stator vane. At step 708, when it is verified that the value of event duration is greater than the event duration threshold, than the control is transferred to step 712. At step 712, it may be declared that an anomaly, a crack or an incipient crack is present.

With returning reference to step 710, one or more of the features 702 may be classified into corresponding one or more clusters. In one embodiment each of the features 702 may be classified into clusters. In one embodiment, when the feature 'amplitude' is classified into clusters, then the clusters may be similar to the clusters 606, 608, 610 explained with reference to FIG. 6. The clusters of the feature 'amplitude', for example, are similar to the clusters 606, 608, 610 with respect to amplitude. For example, each of features 702 may be classified into clusters using pattern recognition techniques. The pattern recognition techniques, for example, may include k-Nearest neighbor technique, and the like.

At step 714, a check is carried out to determine whether the clusters represent background noise, electrical noise, or rub. At step 714 when it is determined that the clusters represent background noise, electrical noise, or rub due to rotating parts, then the control may be transferred to step 720. At step 720, the execution of the method 700 is stopped. However, at step 714 when it is determined that the clusters do not represent background noise, electrical noise or rub, the then the control is transferred to step 712. As previously noted, at step 712 it is declared that an anomaly, crack or incipient crack is present.

Figure 8:
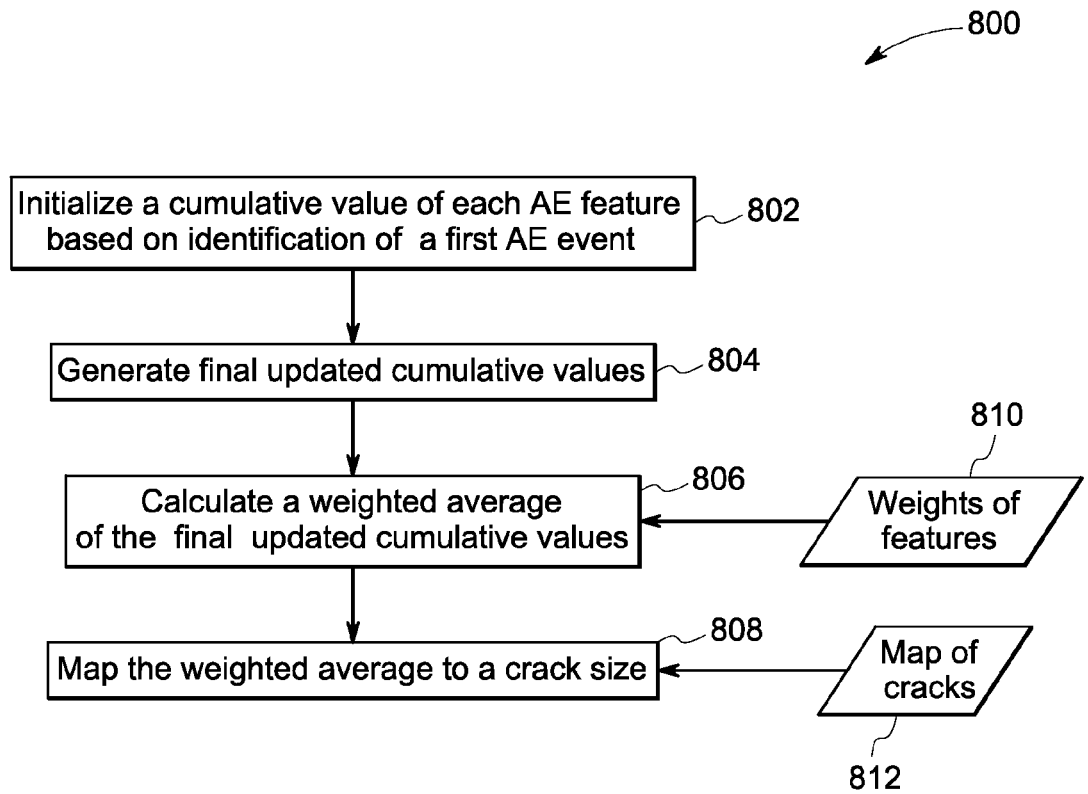
FIG. 8 is an exemplary flow diagram that shows determination of the length of a crack in a stator vane, in accordance with an embodiment of the present techniques.

FIG. 8 is an exemplary flow diagram 800 that shows determination of the length of a crack in a stator vane, in accordance with an embodiment of the present techniques. At step 802, a cumulative value corresponding to each feature may be initialized. The cumulative value, for example, may be initialized at the first instance when an acoustic emission event is detected. The acoustic emission event, for example, may include a detection of an anomaly, a detection of crack or a detection of an incipient crack in a stator vane. For example, a cumulative value corresponding to amplitude may be initialized equal to 'Null'. Also, in another embodiment, the cumulative value corresponding to amplitude may be initialized equal to the value of amplitude at the time instance when the first AE event is detected.

At step 804, the cumulative value corresponding to each AE feature may be iteratively updated on identification of subsequent AE events. Therefore, in the first iteration of method 800, the initialized cumulative value of each AE feature may be added to a corresponding value of a feature on identification of an AE event. For example, if an initialized cumulative value corresponding to a feature F is equal to 'a'. Furthermore, when a subsequent AE event is detected, the value of the feature amplitude is a1, then the cumulative value may be updated to a value equal to 'a+a1' Similarly, when an updated cumulative value corresponding to a feature is a1 in iteration I, and the value of the feature in iteration I+1 is a2, then the updated cumulative value corresponding to the feature may be updated to a1+a2. It is noted that the step 804 may be iterated till a predetermined time. Consequent to the execution of the step 804 till the predetermined time, a final updated cumulative value corresponding to each feature is determined. Subsequently at step 806, a weighted average of the final updated cumulative values may be determined. The weighted average, for example, may be determined based upon predetermined weights 810 assigned to each feature. As used herein, the term "weight of a feature" is used to refer to a degree of importance assigned to each feature. Subsequently at step 808, the weighted average may be mapped to a crack length in a map of cracks 812. The map of cracks includes weighted average values that are mapped to crack lengths. Consequent to the mapping of the crack length to a weighted average value, the length of a crack is determined.

Figure 9:
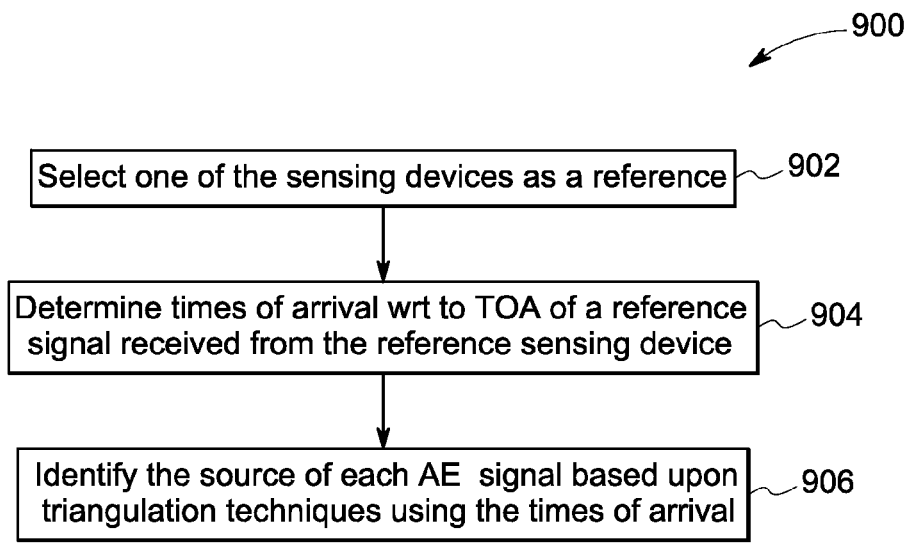
FIG. 9 is an exemplary flow diagram that shows determination of the location of a crack among a plurality of stator vanes.

FIG. 9 is an exemplary flow diagram that shows determination of the location of a crack among the plurality of stator vanes 12. As shown in FIG. 9, at step 902, a sensing device is selected from a plurality of sensing devices located on a casing of a compressor as a reference sensing device. The plurality of sensing devices, for example, may be the sensing devices 18, 20. At step 904, times of arrival of AE signals from the plurality of sensing devices may be determined with respect to the times of arrival of AE signals received from the reference sensing device. Furthermore, at step 906, a source sensing device corresponding to each AE signal may be determined based upon the times of arrival of the AE signals determined at step 904. The source sensing devices, for example, may be determined by applying triangulation techniques on the times of arrival of the AE signals.

The invention claimed is:

1. A system, comprising:
a plurality of sensing devices configured to generate acoustic emission (AE) signals that are representative of acoustic emission waves propogating through a plurality of stator vanes;
a processing subsystem that is in an operational communication with the plurality of sensing devices, and the processing subsystem is configured to:
generate a dynamic threshold based upon an initial threshold and the AE signals;
determine whether a plurality of signals of interest exist in the AE signals based upon the dynamic threshold;
extract the plurality of signals of interest from the AE signals based upon the dynamic threshold;
determine one or more features corresponding to the plurality of signals of interest; and
analyze the one or more features to monitor and validate the health of the plurality of stator vanes.

2. The system of claim 1, wherein the processing subsystem is configured to monitor the health of the plurality of stator vanes in real-time.

3. The system of claim 1, wherein the plurality of sensing devices is optimally distributed across and on the outer surface of a casing of the plurality of stator vanes using a triangulation technique.

4. The system of claim 1, wherein the plurality of sensing devices comprises a piezoelectric sensing device, a magnetostrictive sensing device, an optical sensing device, an acoustic emission sensing device, a radio frequency wireless sensing device, or combinations thereof.

5. The system of claim 1, wherein the processing subsystem is configured to analyze the one or more features using a cumulative analysis technique and a pattern recognition technique.

6. The system of claim 1, wherein the processing subsystem is configured to monitor the health of the stator vanes to determine a crack, an incipient crack or an anomaly in the plurality of stator vanes in real-time.

7. The system of claim 6, wherein the processing subsystem is further configured to determine a length of the crack in one or more of the plurality of stator vanes.

8. The system of claim 7, wherein the processing subsystem is configured to determine the length of the crack by:
initializing a cumulative value corresponding to each of the one or more features on identification of an acoustic emission event;
generating a final cumulative value corresponding to each of the one or more features based upon the initialized cumulative value corresponding to each of the one or more features;
calculating a weighted average of the final cumulative value corresponding to each of the one or more features; and
determining the length of the crack by mapping the weighted average to a determined length.

9. The system of claim 1, wherein the one or more features comprise ring down count (RDC), amplitude, event duration (ED), peak amplitude (PA), rise time (RT), energy, frequency, frequency distribution of the power spectral density, acoustic emission features, or combinations thereof.

10. The system of claim 1, wherein the processing subsystem generates the dynamic threshold in real-time.

11. A method of monitoring the health of a plurality of stator vanes, comprising:
generating acoustic emission (AE) signals that are representative of acoustic emission waves propogating through one or more of the plurality of stator vanes;
generating a dynamic threshold based upon an initial threshold and the AE signals;
determining whether a plurality of signals of interest exist in the AE signals based upon the dynamic threshold;
extracting the plurality of signals of interest from the AE signals based upon the dynamic threshold;
determining one or more features corresponding to the plurality of signals of interest; and
analyzing the one or more features to monitor the health of the plurality of stator vanes.

12. The method of claim 11, wherein generating the dynamic threshold comprises:
initializing the dynamic threshold to generate an initialized dynamic threshold;
extracting a portion of one of the AE signals based upon a hit lockout time;
determine a root mean square value of the extracted portion of the one of the AE signals; and
updating the dynamic threshold based upon a comparison of the root mean square value and the initialized threshold.

13. The method of claim 12, wherein updating the dynamic threshold comprises adding the root mean square value and the initial threshold or adding a root mean square value corresponding to an extracted portion of AE signal and a previously updated dynamic threshold.

14. The method of claim 12, further comprising updating the dynamic threshold based upon a comparison of the root mean square value and a previously updated dynamic threshold.

15. The method of claim 11, wherein analyzing the one or more features comprises cumulative analysis of the one or more features.

16. The method of claim 11, wherein analyzing the one or more features comprises comparing the one or more features with a corresponding threshold.

17. The method of claim 16, wherein analyzing the one or more features further comprises:
- classifying the one or more features into one or more clusters using a pattern recognition technique;
- conducting a check based on turbine operational data to identify whether the one or more clusters represent a gas turbine background noise, electrical noise or a rub noise; and
- identifying an anomaly or a crack or an incipient crack in the one or more of the plurality of stator vanes based upon the check.

18. The method of claim 11, further comprising determining the length of a crack by:
- initializing a cumulative value corresponding to each of the one or more features on identification of an acoustic emission event;
- generating a final cumulative value corresponding to each of the one or more features based upon the initialized cumulative value corresponding to each of the one or more features;
- calculating a weighted average of the final cumulative value corresponding to each of the one or more features; and
- determining the length of the crack by mapping the value of the weighted average to a determined length.

19. The method of claim 18, wherein the acoustic emission event comprises detection of an anomaly, a crack or an incipient crack in the one or more of the plurality of stator vanes.

20. The method of claim 18, wherein generating the final cumulative value comprises iteratively updating the cumulative value corresponding to each of the one or more features on identification of subsequent acoustic emission events till a predetermined time period.

\* \* \* \* \*